US007077652B2

(12) United States Patent
Kilcher et al.

(10) Patent No.: US 7,077,652 B2
(45) Date of Patent: Jul. 18, 2006

(54) CHEEK AND LIP RETRACTOR FOR DENTISTRY

(75) Inventors: Beat Kilcher, Bosco Luganese (CH); Anthony Quarry, Caslano (CH)

(73) Assignee: KerrHawe SA, Bioggio (CH)

( * ) Notice: Subject to any disclaimer, the term of this patent is extended or adjusted under 35 U.S.C. 154(b) by 76 days.

(21) Appl. No.: 10/803,138

(22) Filed: Mar. 17, 2004

(65) Prior Publication Data

US 2004/0209225 A1   Oct. 21, 2004

(30) Foreign Application Priority Data

Mar. 17, 2003   (CH) ..................................... 0432/03

(51) Int. Cl.
A61C 5/00 (2006.01)
(52) U.S. Cl. ....................... 433/140; 433/136; 600/237
(58) Field of Classification Search ................ 433/140, 433/93, 136; 128/200.26; 600/201, 235, 600/237, 238; 482/11; D24/135
See application file for complete search history.

(56) References Cited

U.S. PATENT DOCUMENTS

| 1,742,080 | A | * | 12/1929 | Jones ........................... 433/94 |
| 4,889,490 | A | * | 12/1989 | Jenkinson .................... 433/136 |
| 5,199,872 | A | * | 4/1993 | Leal ............................. 433/136 |
| 6,203,471 | B1 | * | 3/2001 | Akihiro ........................ 482/11 |
| 6,500,002 | B1 | * | 12/2002 | Horiguchi .................... 433/140 |
| 6,743,017 | B1 | * | 6/2004 | O'Neill ....................... 433/140 |
| D496,995 | S | * | 10/2004 | Dorfman .................... D24/135 |
| 6,923,761 | B1 | * | 8/2005 | Dorfman .................... 600/237 |

FOREIGN PATENT DOCUMENTS

| DE | 422 782 | 12/1925 |
| DE | 444 924 | 5/1927 |
| DE | 828 286 | 1/1952 |
| DE | 828 287 | 3/1952 |
| DE | 12 93 947 B | 4/1969 |
| FR | 1 323 843 | 4/1962 |
| FR | 2 645 734 | 4/1989 |
| JP | 10108834 A | 4/1998 |
| NE | 283776 | 9/1962 |
| WO | WO 02 07636 A1 | 1/2002 |

OTHER PUBLICATIONS

International Search Report CH 4322003.

* cited by examiner

Primary Examiner—Melba N. Bumgarner
Assistant Examiner—Jonathan Werner
(74) Attorney, Agent, or Firm—Wood, Herron & Evans, LLP

(57) ABSTRACT

The cheek and lip retractor for dentistry comprises respective cheek portions and lip portions for the upper and lower lip, the lip portions comprising a lip shield and mucous pads which are separate and spaced apart from the lip shield, the cheek portions and lip portions being connected to each other by flexible connecting elements, and the connecting elements being disposed between the lip shield and the mucous pad. Such a retractor allows a largely free treatment of the tooth portions to be treated and provides a comfortable fit for the patient.

6 Claims, 1 Drawing Sheet

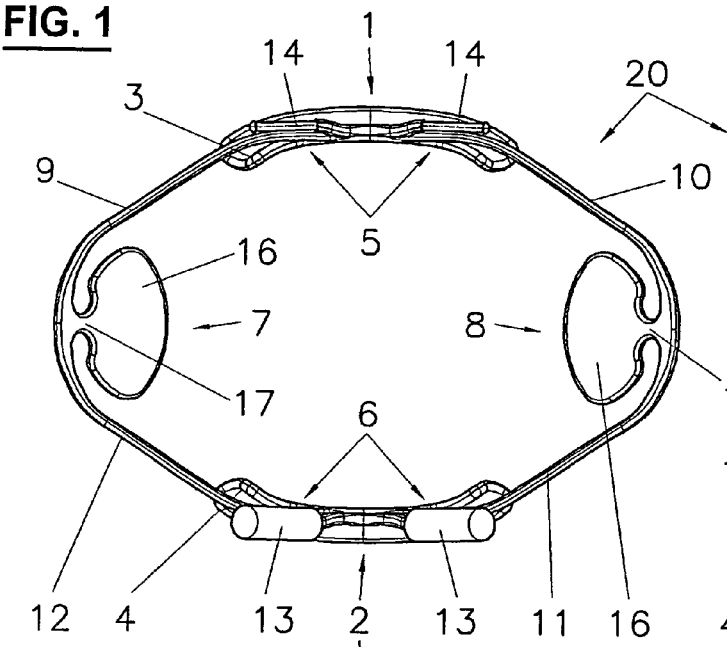
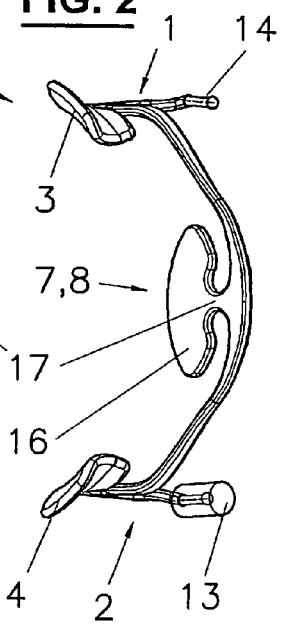
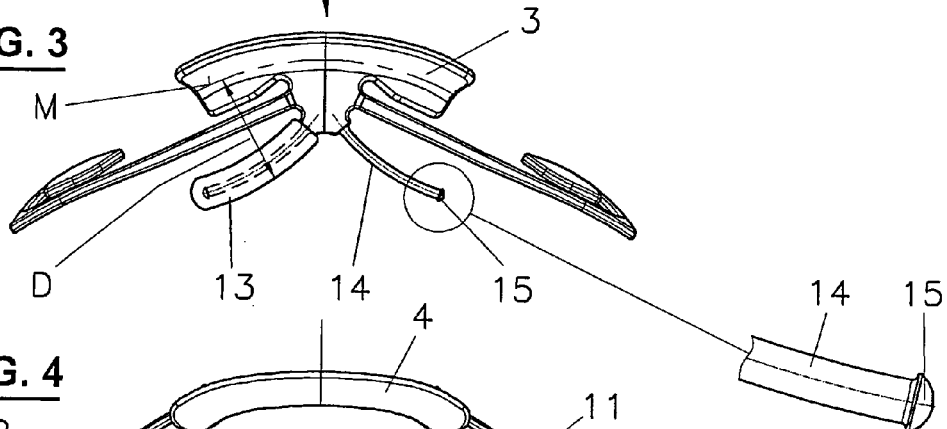
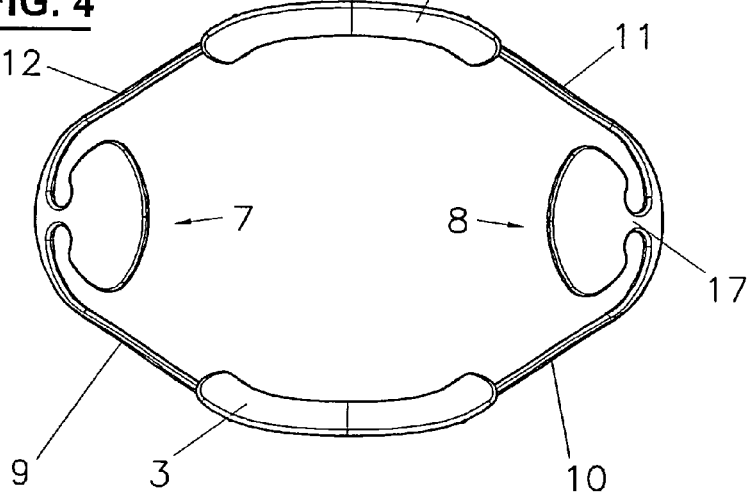

CHEEK AND LIP RETRACTOR FOR DENTISTRY

FIELD OF THE INVENTION

The present invention relates to a cheek and lip retractor for dentistry, intended for retracting the soft tissue in the area of the operating field during treatments in the oral cavity and more particularly on the teeth.

PRIOR ART

A large number of cheek and lip retractors are known in the art, e.g. From U.S. Pat. No. 4,053,984, the retractor disclosed in this reference essentially consisting of a U-shaped bent piece both ends of which are provided with lip shields while the cheeks are pulled out by the U's legs. Through this arrangement, in the area of the mouth corners, the lips are seized as by a rigid hook, thereby making it impossible for the operator to further stretch the mouth corner if necessary. Moreover, the access to the adjacent gingival tissue is insufficient.

Still other retractors are known in the art, which also suffer from the mentioned drawbacks, and where the lip tension resulting from the extension of the lips in the horizontal direction is so strong that it may be uncomfortable for the patient and painful after a time. Also, the retractors of the prior art do not offer sufficient access to the treated surfaces in the area of the front teeth.

SUMMARY OF THE INVENTION

On the background of this prior art, it is the object of the present invention to provide a cheek and lip retractor which eliminates the drawbacks described above and allows to spread the lips in such a manner as to ensure a free access to the areas to be treated, and which is so designed that even a prolonged application of the retractor is not uncomfortable or even painful for the patient.

This is accomplished by a cheek and lip retractor comprising respective cheek portions and lip portions for the upper and lower lip, said lip portions comprising a lip shield and mucous pads which are separate and spaced apart from said lip shield, said cheek portions and lip portions being connected to each other by flexible connecting elements, and said connecting elements being disposed between said lip shield and said mucous pad. Further developments and advantages are set forth in the dependent claims.

BRIEF DESCRIPTION OF THE DRAWINGS

The invention shall be explained in more detail hereinafter with reference to an exemplary embodiment.

FIG. 1 shows a retractor according to the invention in rear view;

FIG. 2 shows the retractor of FIG. 1 in side view;

FIG. 3 shows a detail on an enlarged scale; and

FIG. 4 shows the retractor of FIG. 1 in front view.

DETAILED DESCRIPTION OF THE INVENTION

FIG. 1 shows retractor 20 in rear view with the two lip portions 1 and 2, each provided with respective lip shields 3 resp. 4 and mucous pads 5 resp. 6, as well as the two cheek portions 7 and 8. The lip and cheek portions are arranged in a slightly curved plane and connected to each other by flexible connecting elements 9, 10, 11, 12.

As appears in FIG. 3, the mucous pads comprise respective pairs of rolls 13 that may e.g. be made of silicone or of another suitable material and that are hollow for being slipped on flexible holders 14. It is thus possible to provide rolls of different diameters to ensure an optimal adjustment of the retractor and allow easy cleaning resp. sterilization. The end of holder 14 comprises a thickened portion 15 providing a secure retention of the roll.

As appears especially in FIG. 3, the mucous pads and the lip shield are separated and spaced apart from each other perpendicularly to the plane of the connecting elements. The connecting elements are arranged approximately centrally between the respective mucous pad, the mucous membrane and the lip shield. The distance between the point of support of the mucous pad on the mucous membrane and the center line M of the lip shield is D. This distance may range from 10 mm to 30 mm. The lips are thus lifted off from the teeth in such a manner that a free treatment of the teeth and of the gingival tissue is possible.

The lip shield is anatomically shaped and designed to accommodate different lip shapes, and it is furthermore curved in such a way that it is avoided that the lip is pressed outwards.

The cheek portion is of a flexible construction and includes a curved surface 16 connected to the connecting elements by a flexible web 17. The cheeks are thus retracted from the teeth and from the mucous membrane, and the curved, flexible surfaces provide a high comfort.

The horizontal distance between the cheek portions as well as their dimensions are chosen such that they do not obstruct the area of the mouth corners, and the flexible connecting elements enable the dentist to further spread the mouth corners if required for certain operations. When closing the mouth, the lip portions perform an essentially translational movement. On one hand, the flexible connecting elements assist the requirement of keeping the mouth open, whereby the retractor does not become uncomfortable even in prolonged sessions, but on the other hand, they allow working with the mouth closed.

The entire retractor, except the mucous rolls, may be made in one piece. If the retractor is intended to be reused, synthetic materials available under the designations "PEEK" and "PPSU" have been found to be appropriate, or e.g. "PC" for single use.

Providing the lip portion with mucous pads and designing the cheek portions as flexible surfaces results in a preferred embodiment which offers a comfortable fit for the patient and allows an optimum treatment by the dentist.

The invention claimed is:

1. A cheek and lip retractor for dentistry, comprising respective cheek portions and lip portions for the upper and lower lip, each of said lip portions comprising a lip shield and a pair of mucous pads which are separate and spaced apart from said lip shield, each said lip shield defining a first curved surface for receiving the lip of a patient therein, each said mucous pad comprising an elongate arm having a first axial end coupled to said lip shield and a second axial end cantilevered from said lip shield for contacting a mucous membrane of the patient, whereby the lip of the patient will be lifted and spaced from the teeth and gingival tissue when installed in the patient's mouth, each of said cheek portions being connected to each of said lip portions by a flexible connecting element between said lip shield and one of said pair of mucous pads, each mucous pad comprising a roll axially slipped on a respective one of said elongate arms.

2. The retractor of claim 1, wherein said lip and cheek portions as well as said connecting elements are arranged in a curved plane.

3. The retractor of claim 1, wherein the point of support of said mucous pads on a mucous membrane and the center line of said lip shield are located at a distance from each other.

4. The retractor of claim 3, wherein said distance is in the range of approximately 10 mm to approximately 30 mm.

5. The retractor of claim 1, wherein said cheek portions are in the form of flexible surfaces that are each connected to said connecting elements by a respective flexible web.

6. The retractor of claim 1, wherein said connecting elements are arranged and designed such that in its applied state said lip portions perform an essentially translational movement when closing the mouth.

* * * * *

UNITED STATES PATENT AND TRADEMARK OFFICE
CERTIFICATE OF CORRECTION

PATENT NO. : 7,077,652 B2
APPLICATION NO. : 10/803138
DATED : July 18, 2006
INVENTOR(S) : Kilcher et al.

It is certified that error appears in the above-identified patent and that said Letters Patent is hereby corrected as shown below:

Title Page, Item (57), line 3 and 7-8
reads "...a lip shield and mucous pads which are..." and should read -- ...a lip shield and mucosa pads which are... --
reads "...and the mucous pad." and should read -- "...and the mucosa pad. --.

Column 1
Line 14, reads "...e.g. From U.S. Pat No. ..." and should read -- ...e.g. from U.S. Pat No. ... --.
Line 44, reads "...and mucous pads which are separate..." and should read -- ...and mucosa pads which are separate... --.
Line 47, reads "...and said mucous pad." and should read -- ...and said mucosa pad. --.
Line 66, reads "...and mucous pads 5 resp. 6, as well as..." and should read -- ...and mucosa pads 5 resp. 6, as well as... --.

Column 2
Line 3, reads "...the mucous pads comprise..." and should read -- ...the mucosa pads comprise... --.
Line 11, reads "...the mucous pads and the..." and should read -- ...the mucosa pads and the... --.
Line 15, reads "...between the respective mucous pad, the..." and should read -- ...between the respective mucosa pad, the... --.
Line 17, reads "...of the mucous pad on the mucous membrane..." and should read -- ...of the mucosa pad on the mucous membrane... --.
Line 42, reads "...except the mucous rolls, may be made..." and should read -- ...except the mucosa rolls, may be made... --

Line 47, reads "...portion with mucous pads and..." and should read -- ...portion with mucosa pads and... --.
Lines 55, 58 and 66, reads "...mucous..." and should read -- mucosa --.

UNITED STATES PATENT AND TRADEMARK OFFICE
CERTIFICATE OF CORRECTION

PATENT NO.       : 7,077,652 B2
APPLICATION NO.  : 10/803138
DATED            : July 18, 2006
INVENTOR(S)      : Kilcher et al.

It is certified that error appears in the above-identified patent and that said Letters Patent is hereby corrected as shown below:

<u>Column 3</u>
Line 5, reads "...mucous..." and should read -- mucosa --.

Signed and Sealed this

Twenty-fourth Day of October, 2006

JON W. DUDAS
*Director of the United States Patent and Trademark Office*